United States Patent [19]

Soga et al.

[11] Patent Number: 5,800,419
[45] Date of Patent: Sep. 1, 1998

[54] DISPOSABLE BODY FLUID ABSORBENT GARMENT

[75] Inventors: Hiroyuki Soga, Kagawa-ken; Noriyuki Kimura, Ehime-ken, both of Japan

[73] Assignee: Uni-Charm Corporation, Ehime-ken, Japan

[21] Appl. No.: 757,795

[22] Filed: Nov. 27, 1996

[30] Foreign Application Priority Data

Nov. 30, 1995 [JP] Japan .................. 7-311912

[51] Int. Cl.⁶ .............. A61F 13/15; B32B 13/20; D04H 1/58
[52] U.S. Cl. .............. 604/368; 604/358; 604/367; 428/284; 428/288; 428/913
[58] Field of Search .................. 604/358, 367, 604/368, 372, 365, 385.1, 385.2, 364, 370, 371, 373, 374, 378, 386, 393–402; 428/284, 288, 913

[56] References Cited

U.S. PATENT DOCUMENTS

| | | |
|---|---|---|
| 4,035,540 | 7/1977 | Ganger .................. 604/368 |
| 4,062,451 | 12/1977 | Gander .................. 604/368 |
| 4,115,332 | 9/1978 | Young et al. .................. 604/368 |
| 5,149,335 | 9/1992 | Kellenberger .................. 604/372 |
| 5,195,999 | 3/1993 | Harada et al. .................. 604/368 |
| 5,346,485 | 9/1994 | Yarbrough et al. .................. 604/368 |

*Primary Examiner*—John G. Weiss
*Assistant Examiner*—Francis K. Cuddihy
*Attorney, Agent, or Firm*—Lowe Hauptman Gopstein Gilman & Berner

[57] ABSTRACT

Superabsorbent polymer particles are used in a liquid-absorbent core of a disposable body fluid absorbent garment. The polymer particles include first polymer particles having a relatively high water-absorption speed and second polymer particles having a water-absorption speed longer than that of the first polymer particles by 10 seconds or more. The second polymer particles are integrally bonded to the first polymer particles.

6 Claims, 3 Drawing Sheets

DISPOSABLE BODY FLUID ABSORBENT GARMENT

BACKGROUND OF THE INVENTION

The present invention relates to a disposable body fluid absorbent garment such as a disposable diaper or a sanitary napkin.

It is well known in a garment of this type to cover a liquid-absorbent core including fluff pulp and superabsorptive polymer particles with a liquid-permeable sheet. It is also well known that superabsorbent polymer particles tend to become viscous and agglomerate together into gel blocks, if they absorb water. Such gel blocks prevent body fluids from permeating into the liquid-absorbent core and may cause the body fluids to leak, when the gel blocks are formed in the top surface area of the core.

One of the measures to prevent the superabsorbent polymer particles from forming such gel blocks is to disperse the superabsorbent polymer particles in such water-absorptive fibrous material such as fluff pulp which is used with the polymer particles so that the individual particles are adequately spaced apart from one another. However, such a measure is not practical due to a limitation imposed upon a size of the liquid-absorbent core. There may occur a case in which the disposed polymer particles cannot be used so effectively as to achieve an effect expected for the liquid-absorbent core. To overcome such a problem, it may be contemplated to mix polymer particles having a relatively high water-absorption speed with polymer particles having a relatively low water-absorption speed. For example, the polymer particles of these two types which are different in their water-absorption speeds are mixed together so that a mixture thereof may form a single layer in a liquid-absorbent core. However, it may be difficult to mix them uniformly them if the polymer particles of these two types are of significantly different particle sizes. It is further contemplated to arrange the polymer particles of these two types to form separate layers in liquid-absorbent core without being mixed together. Thereby the polymer particles having a relatively low water-absorption speed form an upper layer while the polymer particles having a relatively high water-absorption speed form a lower layer and fluff pulp is disposed between these two layers. However, such an arrangement would make the manufacturing process for a liquid-absorbent core complex because the polymer particles must be fed twice in the process.

SUMMARY OF THE INVENTION

In view of problems as have been described above, it is a principal object of the invention to prevent superabsorbent polymer particles from easily forming gel blocks within a liquid-absorbent core.

The object set forth above is achieved, according to the invention, by a disposable body fluid absorbent garment having a liquid-absorbent core comprising a mixture of water-absorptive fibrous material and superabsorbent polymer particles, and a liquid-permeable sheet at least partially covering the liquid-absorbent core. The disposable body fluid absorbent garment is characterized by:

the polymer particles comprise first polymer particles having a water-absorption time shorter than 10 seconds as measured under the conditions a, given below and second polymer particles having a water-absorption time longer than that of the first polymer particles by 10 seconds or more and integrally bonded to the first polymer particles. Measurement conditions for water-absorption time include (1) 25 ml of 0.9% saline water poured into a 50 ml beaker and stirred at 500 r.p.m. by a magnetic stirrer equipped with a rotary element having a diameter of 7 mm and a length of 20 mm; and (2) 1 g of superabsorbent polymer particles is poured into the beaker during stirring and a time required by these polymer particles to absorb the whole quantity of the saline water is determined by visual inspection.

DETAILED DESCRIPTION OF THE INVENTION

Details of the invention will be more fully understood from the following description of a disposable diaper as a specific embodiment of the invention made with respect to the accompanying drawings.

Figure 1:
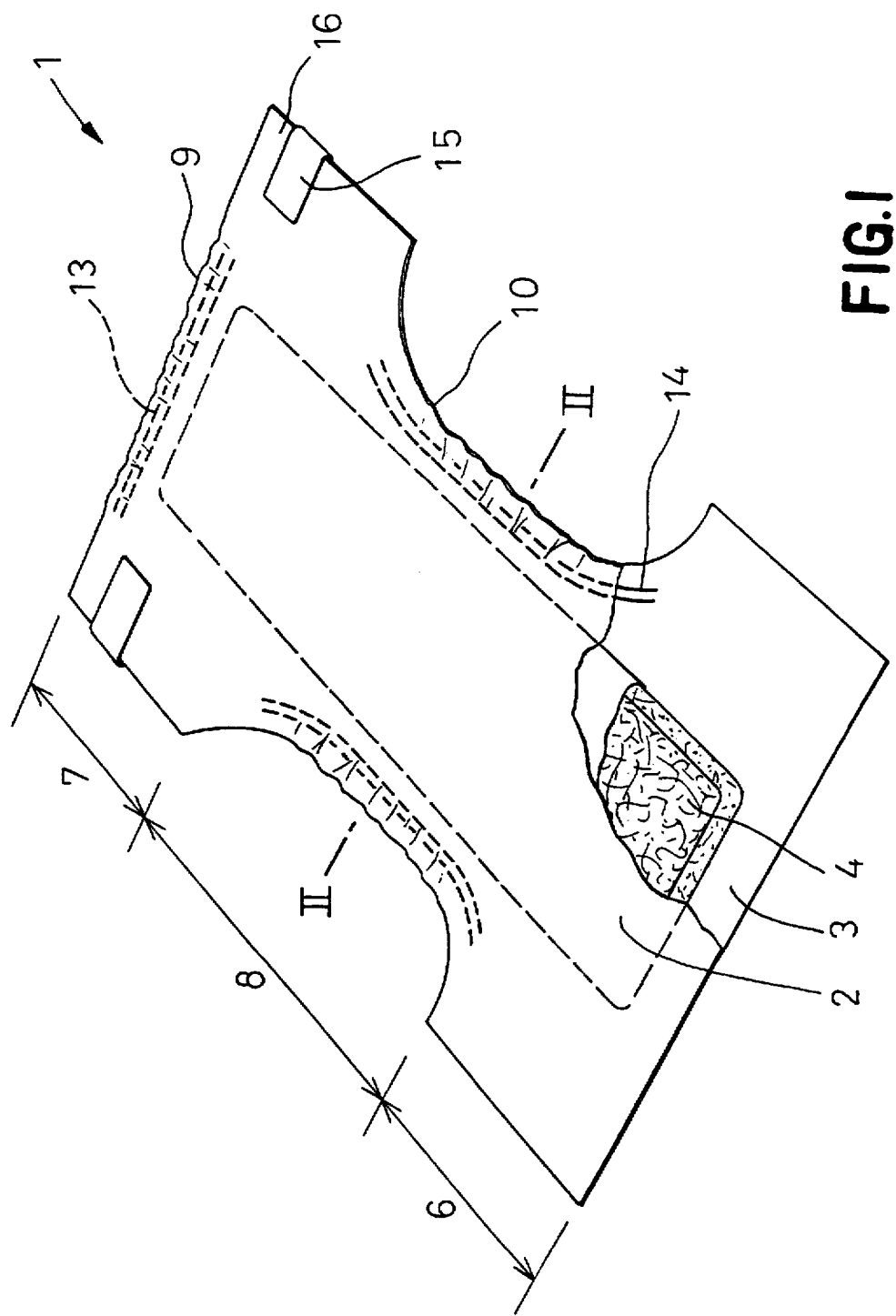
FIG. 1 is a perspective view depicting an embodiment of a disposable diaper of the invention as partially broken away.

A diaper 1 depicted in shown by FIG. 1 in a perspective view as partially broken away comprises a liquid-permeable topsheet 2, a liquid-impermeable backsheet 3, and a liquid-absorbent core 4 disposed between these two Sheets 2, 3. Portions of these two sheets 2, 3 extending outward beyond the whole peripheral edge of the core 4 are put one upon the other and water-tightly bonded to each other. The diaper 1 is longitudinally composed of a front region 6, a rear region 7 and a crotch region 8 extending between these regions 6, 7. Adjacent the upper edge 9 of the rear region 7 and transversely opposite side edges 10 of the crotch region 8, an elastic member 13 for a waist-opening. Elastic members 14 for a pair of leg-openings are respectively disposed between the top- and backsheets 2, 3 and bonded under an elastically stretched condition to an inner surface of at least one of the two sheets 2, 3. Transversely opposite side edges 16 of the rear region 7 are provided with tape fasteners 15.

Figure 2:
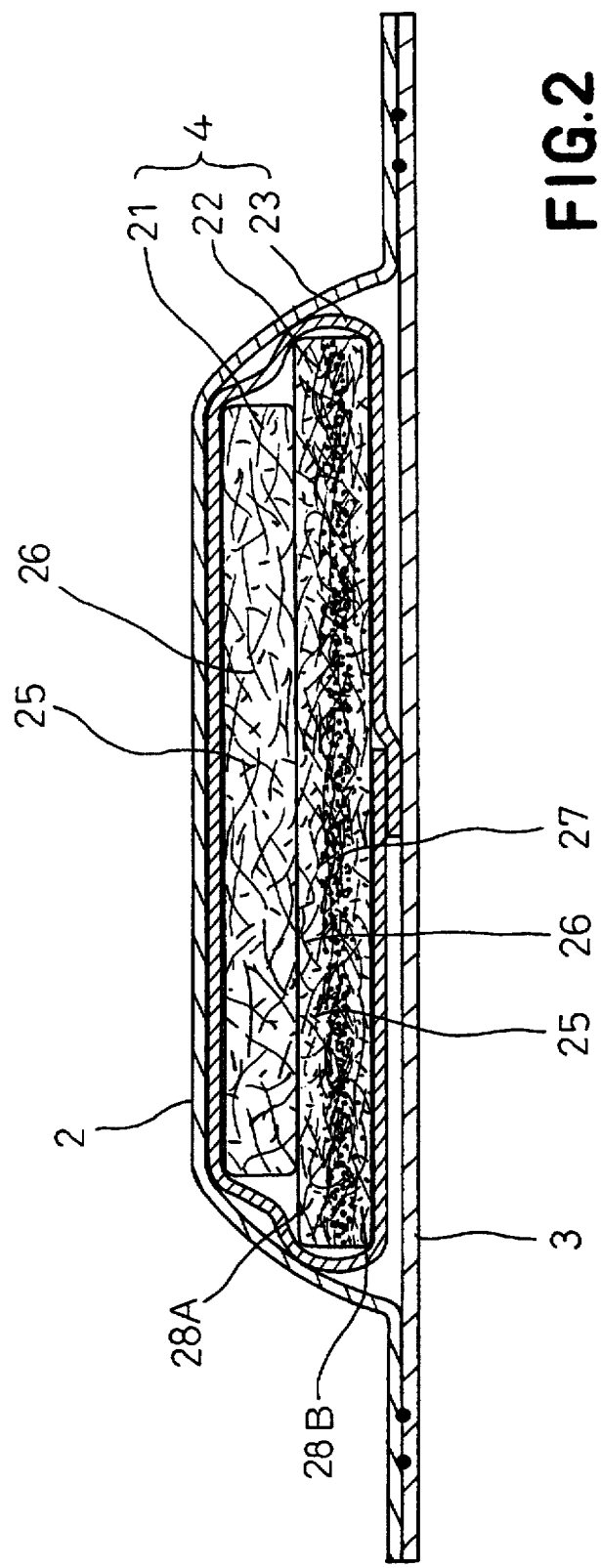
FIG. 2 is a sectional view taken along line II—II in FIG. 1.

FIG. 2 is a sectional view taken along line II—II in FIG. 1. As depicted, the core 4 comprises an upper layer 21, a lower layer 22 and a tissue paper 23 covering the upper and lower layers 21, 22. The upper layer 21 has a basis weight of 190 g/m$^2$ and comprises a mixture of fluff pulp 25 of 90% by weight and thermoplastic fibers 26 of 10% by weight. The lower layer 22 has a basis weight of 430 g/m$^2$ and comprises fluff pulp 25 of 50% by weight, thermoplastic fibers 26 of 5% by weight and superabsorbent polymer particles 27 of 45% by weight. In the lower layer the polymer particles 27 are distributed between a top layer 28A and a bottom layer 28B. These two layers 28A, 28B respectively comprise a mixture of the fluff pulp 25 and the thermoplastic fibers 25. The upper and lower layers 21, 22 are heat-treated so that the thermoplastic fibers 26 may be integrally heat-bonded within each layer 21, 22 as well as between the two layers 21, 22 and thereby prevent a shape-loss of the core 4 as a whole. The tissue paper 23 serves to protect such components as the fluff pulp 25 against scattering and at the same time to facilitate handling of the core 4 during a manufacturing process of the diaper. It should be understood that the tissue paper 23 may be eliminated from the core 4, unless it is necessary.

Figure 3:
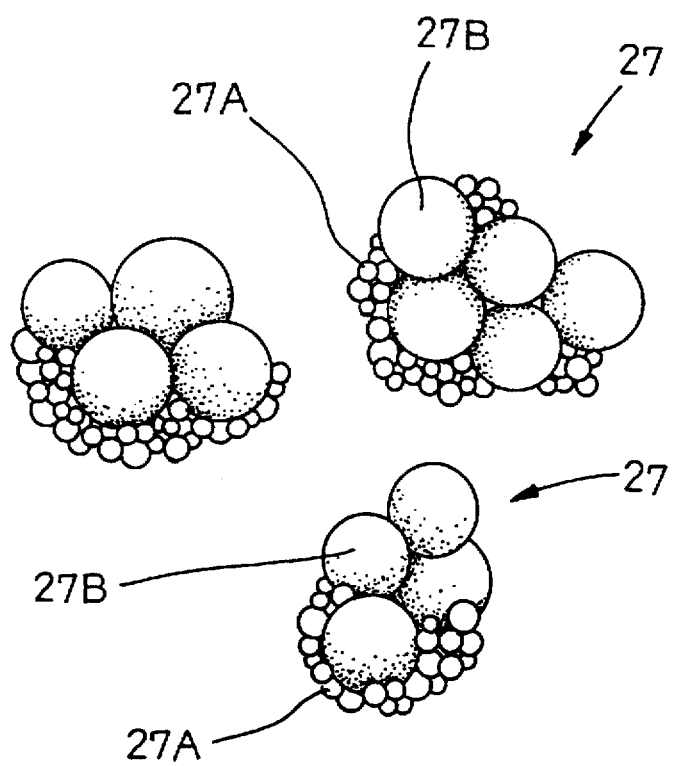
FIG. 3 is a schematic diagram illustrating super-absorbent polymer particles.

The superabsorbent polymer particles 27 schematically illustrated by FIG. 3 in an enlarged scale comprise first polymer particles 27A of a relatively high water-absorption speed and a relatively small particle size and the second polymer particles 27B bonded to the polymer particles 27A and having a relatively low water-absorption speed and a relatively large particle size. The particle sizes of the polymer particles 27 are in a range of 0.2–0.8 mm. The first polymer particles 27A and the second polymer particles 27B should have a differential water-absorption time of 10 or more seconds and the first polymer particles 27A should have a water-absorption time shorter than 10 seconds as measured under the conditions as will be described below.

Measurement conditions for water-absorption time:

(1) 25 ml of 0.9% saline water is poured into a 50 ml beaker and stirred at 500 r.p.m. by a magnetic stirrer equipped with a rotary element having a diameter of 7 mm and a length of 20 mm; and (2) 1 g of superabsorbent polymer particles is poured into the beaker during stirring and a time required by the polymer particles to absorb the whole quantity of the saline water is visually determined.

The polymer particles 27 as a complex of the first and second polymer particles 27A, 27B can be obtained by, for example, adding the second polymer particles 27B to a polymerizing system of water-soluble ethylenic unsaturated monomer to produce the first polymer particles 27A.

A process for producing the polymer particles 27 will be more specifically described. The water-soluble ethylenic unsaturated monomers include nonionic monomers such as (metha)acrylic acid, 2-(metha)acrylamide-2-methylpropane sulfonic acid and alkali salts thereof, (metha)acrylamide, N, N-dimethylacrylamide, 2-hydroxyethyl(metha)acrylate, and N-methylol(metha)acrylamide, and amino-group containing unsaturated monomers such as diethylaminoethyl(metha)acrylate, diethylaminopropyl(metha)acrylate and diethylaminopropyl (metha) acrylamide and quaternary compounds thereof. Two or more of these water-soluble ethylenic unsaturated monomers may be used in the form of a mixture. It should be understood that (metha)acrylic acid and derivatives thereof may be replaced by acrylic acid and derivatives thereof. These water-soluble ethylenic unsaturated monomers are usually used in a state of aqueous solution.

For the water-soluble ethylenic unsaturated monomers a reversed-phase suspension polymerization is applied and suitable hydrocarbon is used as solvent. The hydrocarbon solvent includes aliphatic hydrocarbon solvent, alicyclic hydrocarbon solvent and aromatic hydrocarbon solvent. The aliphatic hydrocarbon solvent includes n-hexane, n-heptane and ligroine. The alicyclic hydrocarbon solvent includes cyclopentane, methylcyclopentana, cyclohexane and methylcyclohexane. The aromatic hydrocarbon solvent includes benzene, toluene and xylene. These hydrocarbon solvents may be used in the form of a mixture of two or more hydrocarbon solvents.

During the reversed-phase suspension polymerization, the hydrocarbon solvent is added with surfactant or macromolecule protective colloidal. These surfactant and macromolecule protective colloid may be used together. The surfactant may be selected from those which allow for reversed-phase suspension polymerization of water-soluble ethylenic unsaturated monomer, for example, nonionic surfactants such as sorbitan fatty acid ester, polyglycerin fatty acid ester, sucrose fatty acid ester, sorbitol fatty acid ester, polyoxyethylenealkylphenyleter. The macromolecule protective colloids include ethylcellulose, ethylhydroxethylcellulose, oxidation-modified polyethylene, maleic anhydride-modified polyethylene, maleic anhydride-modified polybutadiene, maleic anhydride-modified EPDM (ethylene propylene diene terpolyifter).

These nonionic surfactant and macromolecule protective colloid may be used with anionic surfactant such as salts of fatty acid, alkylbenzenesulfonic acid, alkylmethyltaurine, polyoxyethylenealkylphenylether sulfuric acid ester or polyoxyethylenealkylether sulfonic- acid. Effective quantity of surfactant and/or macromolecule protective colloid is usually 0.1–5% by weight and more preferably 0.2–3% by weight of aqueous solution of water-soluble ethylenic unsaturated monomer.

For polymerization of water-soluble ethylenic unsaturated monomer, suitable crosslinking agents may be used. Such crosslinking agents include: di- or tri-(metha) acrylic acid esters of polyols such as ethylene glycol, propylene glycol, trimethylolpropane, glycerinpolyoxyethylene glycol, polyoxypropylene glycol, polyglycerin; or unsaturated polyesters obtained from reaction of these polyols with unsaturated acids such as maleic acid and fumaric acid; bis-acrylamides such as N, N'-methylenebisacrylamide; di- or tri(metha) acrylic acid esters obtained from reaction of polyepxide with (metha)acrylic acid; di-(metha)acrylic acid carbamyl esters obtained from reaction of polyisocyanates such as tolylene di-isocyanate, hexamethylene diisocyanate with (metha) acrylic acid hydroxyethyl; allyl starch; allyl cellulose; diallylphthalate; N, N', N"-triallylisocynurate; and divinylbenzene. The crosslinking agents further include, for example, diglycidylether compounds, haloepoxy compounds and isocyanate compounds. Effective quantity of such crosslinking agents is 0.001–5% by weight of water-soluble ethylenic unsaturated monomer.

For polymerization reaction, any suitable radical polymerization initiators can be used. The initiators include water-soluble radical initiators such as potassium persulfate, ammonium persulfate and sodium persulfate, and oil-soluble radical initiators such as benzoyl peroxide and azobisisobutyronitrile. Effective quantity of these initiators is 0.005–1.0% by mol.

A temperature at which the polymerization is carried out usually in the range of 20°–110°C. and preferably in the range of 40°–80°C. depending on the initiators to be used.

Commercial water-absorbent polymers could be adapted as the superabsorbent polymer particles to be added to the polymerizing system of water-soluble ethylenic unsaturated monomer. More specifically, such polymers include starch containing water-absorbent polymers such as hydrolysate of starch-acrylonitrile graft copolymer and neutralized product of starch-acrylic acid graft copolymer, saponified product of vinyl acetate-acrylic acid ester copolymer, partially neutralized product of polyacrylic acid, maleic anhydride-isobutylene copolymer and polymerized product from water-soluble ethylenic unsaturated monomer.

Effective quantity of superabsorbent polymer particles to be added to the polymerization system is in the range of 5–50% by weight of water-soluble ethylenic unsaturated monomer contained in this system.

The water-absorbent polymer particles may be added to the aqueous solution of water-soluble ethylenic unsaturated monomer before the polymerization starts or further added to the polymerization system after the water-soluble ethylenic unsaturated monomer has been dispersed into the hydrocarbon solvent.

The garment of the present invention includes superabsorbent polymer particles comprising the first polymer particles having a relatively high water-absorption speed and the second polymer particles having a water-absorption speed lower than that of the first polymer particles by 10 seconds or more and integrally bonded to the first polymer particles. With such a complex of superabsorbent polymer particles, when body fluids flow into a layer formed by plenty of the polymer particles being closely in contact with one another, part of the body fluids is absorbed by the first polymer particles located in a surface zone of the layer. As a result, the first polymer particles are swollen and tend to prevent the body fluids from further permeating downward. On the other hand, the second polymer particles having a relatively low water-absorption speed are not easily swollen and provide among the swollen first polymer particles with voids allowing the body fluids to pass through. The body fluids come into contact with the first polymer particles underlying the voids and are absorbed by the particles. In this manner, the presence of the second polymer particles effectively to prevent the layered superabsorbent polymer particles from forming gel blocks in the surface zone of the lower layer. Thus, the first polymer particles underlying the surface zone can be effectively used.

What is claimed is:

1. A disposable body fluid absorbent garment comprising a liquid-absorbent core including a mixture of water-absorbent fibrous material and superabsorbent polymer particles and a liquid-permeable sheet at least partially covering the liquid-absorbent core;

wherein the polymer particles comprise first polymer particles having a water-absorption time shorter than 10 seconds as measured under the conditions as given below and second polymer particles having a water-absorption time longer than that of said first polymer particles by 10 seconds or more, said second polymer particles being integrally bonded to the first polymer particles;

whereby measurement conditions for water-absorption time include:

(1) 25 ml of 0.9% saline water is poured into a 50 ml beaker and stirred at 500 r.p.m. by a magnetic stirrer equipped with a rotary element having a diameter of 7 mm and a length of 20 mm; and (2) 1 g of superabsorbent polymer particles is poured into the beaker during stirring and the time required by the polymer particles to absorb the whole 25 ml of saline water is determined by visual inspection.

2. The disposable body fluid absorbent garment according to claim 1, wherein said core comprises an upper layer and a lower layer.

3. The disposable body fluid absorbent garment according to claim 2, wherein said upper layer includes a mixture of fluff pulp and thermoplastic fibers.

4. The disposable body fluid absorbent garment according to claim 3, wherein said mixture includes fluff pulp of about 90% by weight and thermoplastic fibers of about 10% by weight.

5. The disposable body fluid absorbent garment according to claim 2, wherein said lower layer includes a mixture of fluff pulp, thermoplastic fibers, and superabsorbent polymer particles.

6. The disposable body fluid absorbent garment according to claim 5, wherein said mixture includes fluff pulp of about 50% by weight, thermoplastic fibers of about 5% by weight, and superabsorbent polymer particles of about 45% by weight.

* * * * *